(12) United States Patent
White et al.

(10) Patent No.: US 7,798,963 B2
(45) Date of Patent: Sep. 21, 2010

(54) METHOD FOR SYNCHRONIZATION OF BREATHING SIGNAL WITH THE CAPTURE OF ULTRASOUND DATA

(75) Inventors: Chris A. White, Toronto (CA); James I. Mehi, Thornhill (CA); Desmond Hirson, Thornhill (CA)

(73) Assignee: VisualSonics Inc., Toronto (CA)

( * ) Notice: Subject to any disclaimer, the term of this patent is extended or adjusted under 35 U.S.C. 154(b) by 591 days.

(21) Appl. No.: 11/367,093

(22) Filed: Mar. 3, 2006

(65) Prior Publication Data

US 2006/0241446 A1 Oct. 26, 2006

Related U.S. Application Data

(60) Provisional application No. 60/658,718, filed on Mar. 4, 2005.

(51) Int. Cl.
*A61B 8/00* (2006.01)
(52) U.S. Cl. ........................... 600/437; 600/443
(58) Field of Classification Search .................. 600/437
See application file for complete search history.

(56) References Cited

U.S. PATENT DOCUMENTS

| | | | |
|---|---|---|---|
| 4,926,875 A | 5/1990 | Rabinovitz et al. | |
| 4,947,854 A | 8/1990 | Rabinovitz et al. | |
| 5,271,055 A | 12/1993 | Hsieh et al. | |
| 6,013,031 A | 1/2000 | Mendlein et al. | |
| 6,228,028 B1 | 5/2001 | Klein et al. | |
| 6,511,426 B1 | 1/2003 | Hossack et al. | |
| 6,689,060 B2 * | 2/2004 | Phelps et al. | 600/437 |
| 6,704,593 B2 | 3/2004 | Stainsby et al. | 600/413 |
| 6,705,992 B2 | 3/2004 | Gatzke | |
| 6,755,787 B2 | 6/2004 | Hossack et al. | |
| 6,795,585 B1 * | 9/2004 | Parada et al. | 382/254 |
| 6,951,540 B2 * | 10/2005 | Ebbini et al. | 600/437 |
| 7,010,163 B1 * | 3/2006 | Weiss | 382/168 |
| 7,182,083 B2 | 2/2007 | Yanof et al. | |
| 2002/0007119 A1 * | 1/2002 | Pelissier | 600/443 |
| 2003/0188757 A1 * | 10/2003 | Yanof et al. | 128/916 |
| 2004/0236219 A1 * | 11/2004 | Liu et al. | 600/437 |
| 2004/0249264 A1 | 12/2004 | Salgo et al. | |

(Continued)

FOREIGN PATENT DOCUMENTS

WO    WO 2004/062501    7/2004

(Continued)

OTHER PUBLICATIONS

Ranault et al. "A Posteriori Navigator Echo for Perfusion Imaging of the Liver With Contrast Ultrasound," Biomedical Imaging: Macro to Nano, 2004. IEEE International Symposium Apr. 15-18, 2004; vol. 1, pp. 316-319.

(Continued)

*Primary Examiner*—Long V Le
*Assistant Examiner*—Hien Nguyen
(74) *Attorney, Agent, or Firm*—Clark & Elbing LLP; Kristina Bieker-Brady (57) ABSTRACT

A method for producing an ultrasound image comprises monitoring the subject's respiration cycle or waveform, acquiring ultrasound data from the subject, producing an ultrasound image from the received ultrasound data received during the time when the subject's motion due to breathing had substantially stopped.

13 Claims, 9 Drawing Sheets

U.S. PATENT DOCUMENTS

| | | | |
|---|---|---|---|
| 2005/0039699 | A1 | 2/2005 | Sato et al. |
| 2005/0251232 | A1 | 11/2005 | Hartley et al. |
| 2006/0241461 | A1 | 10/2006 | White et al. |

FOREIGN PATENT DOCUMENTS

| | | |
|---|---|---|
| WO | WO 2004/099814 | 11/2004 |
| WO | WO 2010/033867 | 3/2010 |

OTHER PUBLICATIONS

Liu et al., "ECG Gated Ultrasonic Small Animal Imaging," *Proceedings of the 2005 IEEE* 1762-1765, 2005.

Crossland et al., "A Simple Device for Measurement of Respiratory Rate in the Mouse," *Proceedings of the B.P.S.* 490-491P, 1977.

International Search Report for PCT/IB2006/002031 mailed Jan. 12, 2007.

International Preliminary Report on Patentability for PCT/IB2006/002031 issued Sep. 12, 2007.

Supplementary European Search Report for EP 06 79 5158 completed Nov. 3, 2008.

Wagner et al., "Monitoring heart and respiratory activity by impedance change using neck electrodes," *Med. & Biol. Eng. & Comput.* 25:100-102, 1987.

Neonatal respiration monitoring by detection of the diaphragmatic electromyogram (http://medical.ukc.ac.uk/research/neonatal/respiration.html), viewed on Apr. 17, 2006.

U.S. Appl. No. 12/562,935, filed Sep. 18, 2009, Mehi et al.

* cited by examiner

602 — Start

604 — Position Transducer to the start (or left side) of the color box

606 — Capture Respiration Waveform

608 — Wait for respiration peak

610 — Capture data (for example, Doppler data) in the non-motion period

612 — Process data

614 — Step incrementally a scan line

616 — Is the transducer at the right edge of the color box? NO → 610; YES ↓

618 — Stop Process? NO → 604; YES ↓

620 — Finish

METHOD FOR SYNCHRONIZATION OF BREATHING SIGNAL WITH THE CAPTURE OF ULTRASOUND DATA

CROSS-REFERENCE TO RELATED APPLICATIONS

This application claims priority to and the benefit of U.S. Provisional Application No. 60/658,718, filed on Mar. 4, 2005, which are incorporated in their entirety in this document by reference.

BACKGROUND

Small animal or laboratory animal research is a cornerstone of modern biomedical advancement. Research using small animals enables researchers to understand complex biological mechanisms, to understand human and animal disease progression, and to develop new drugs to cure or alleviate many human and animal maladies. Small animal research is important in many areas of biomedical research including neurobiology, developmental biology, cardiovascular research and cancer biology. High-frequency ultrasound and high-frequency Doppler ultrasound can be used to image small animals for biomedical research.

Typically, when producing images of an animal using high-frequency Doppler ultrasound, the animal's breathing motion causes artifacts and inaccuracies in the image. For Doppler measurement of the velocity of blood flowing in a vessel, movement of the vessel due to the animal's breathing motion contributes to erroneous measured velocities. When an image is constructed using an ultrasound technique exploiting the total power in the Doppler signal to produce color-coded real-time images of blood flow ("Power Doppler") over a two-dimensional surface, a motion artifact is displayed as large stripes in the image. Researchers have therefore been limited to producing images of only those parts of the small animal's anatomy not affected by breathing motion. Thus, breathing motion artifacts and inaccuracies hinder beneficial small animal research.

Acquisition of 3D volumes also suffers from respiration artifacts. 3D volumes typically consist of between approximately 2 and 500 individual image frames acquired with a spacing of between approximately 0.01 millimeter (mm) to 1.0 mm. When a number of slices have been acquired they are compiled to render a 3D volume. Each position consists of an independently acquired frame which may consist of a "Power Doppler" frame, a B-Mode frame, or combination of the two. Respiration artifacts cause unwanted motion which reduces the accuracy of the rendered volume.

SUMMARY

According to one embodiment a method for producing an ultrasound image comprises generating ultrasound at a frequency of at least 20 megahertz (20 MHz), transmitting the ultrasound of at least 20 MHz into a subject, monitoring the subject's respiration cycle or waveform, acquiring Doppler, B-Mode, or raw RF ultrasound data from the subject, and producing an ultrasound image from the ultrasound data received during the time when the subject's motion due to breathing has substantially stopped.

Other apparatus, methods, and aspects and advantages of the invention will be discussed with reference to the Figures and to the detailed description of the preferred embodiments.

BRIEF DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "surface"

includes aspects having two or more such surfaces unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention may be understood more readily by reference to the following detailed description of preferred embodiments of the invention and the examples included therein and to the Figures and their previous and following description.

By a "subject" is meant an individual. The term subject includes small or laboratory animals as well as primates, including humans. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

Figure 1:
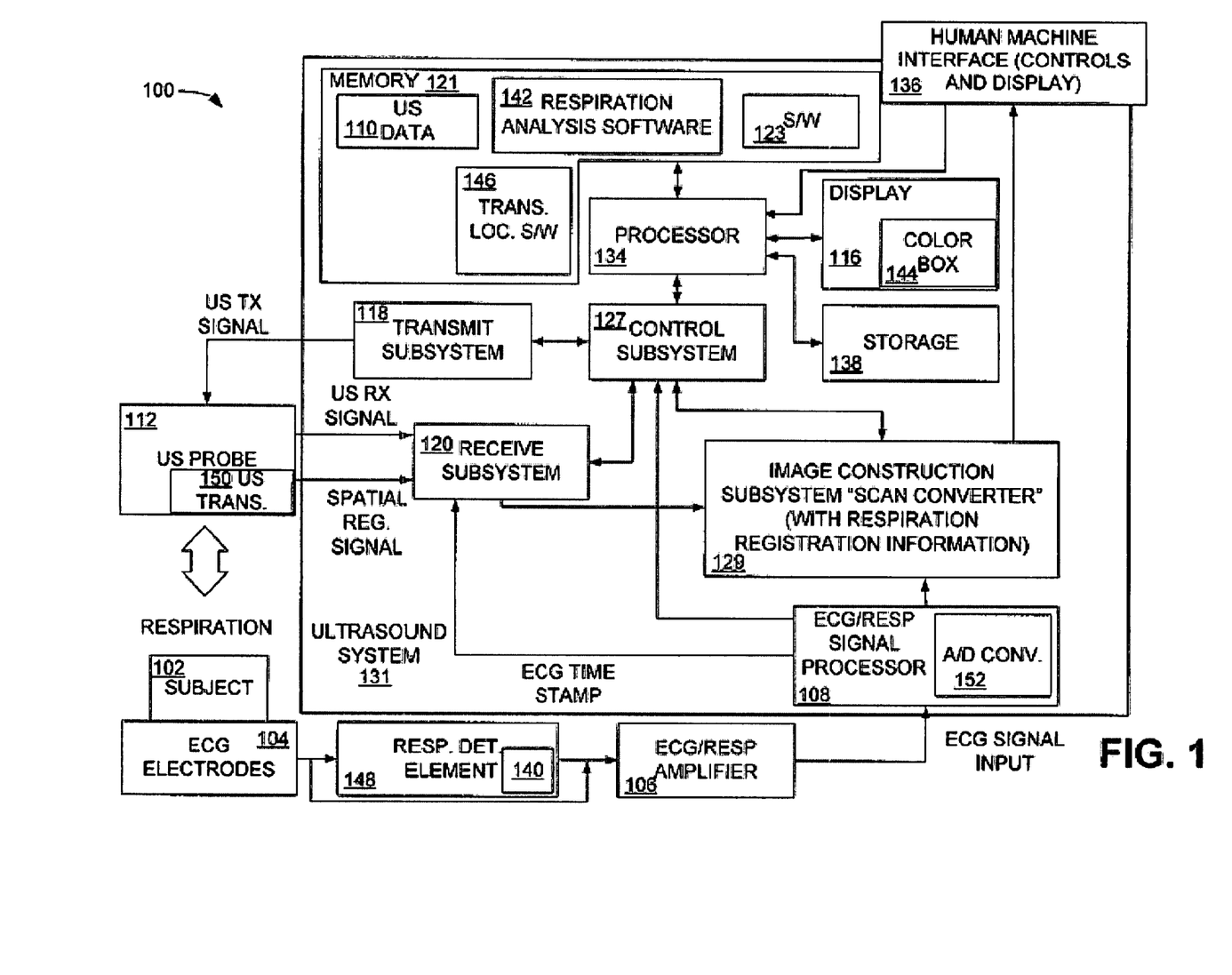
FIG. 1 is a block diagram illustrating an exemplary imaging system.

FIG. 1 is a block diagram illustrating an exemplary imaging system 100. In this aspect, the imaging system 100 operates on a subject 102. An ultrasound probe 112 is placed in proximity to the subject 102 to obtain ultrasound image information. The ultrasound probe can comprise a mechanically moved transducer that can be used for collection of ultrasound data 110, including, for example and not meant to be limiting, Power Doppler ultrasound data, Color Flow velocity ultrasound data, Tissue Doppler data, B-Mode ultrasound data, M-Mode ultrasound data, and raw RF ultrasound data. As noted below, one skilled in the art will appreciate that it is contemplated that the disclosed methods can also be practiced using an array based ultrasound system, exemplarily illustrated the block diagram FIG. 9, in addition to a system comprising a mechanically moved transducer.

It is contemplated that any system capable of translating a beam of ultrasound across a subject or portion thereof could be used to practice the described methods. Thus, the methods can be practiced using a mechanically scanned system that can translate an ultrasound beam as it sweeps along a path, or, alternatively, a plurality of ultrasound beams as it sweeps along the path. The methods can also be practiced using an array based system where a plurality of beams is generated and translated by electrical steering along the elements of the transducer. One skilled in the art will appreciate that beams translated from either type system can be used in the described methods, without any limitation to the type of system employed. Thus, one of skill in the art will appreciate that the methods described as being performed with a mechanically scanned system can also be performed with an array system. Similarly, methods described as being performed with an array system can also be performed with a mechanically scanned system. The type of system is therefore not intended to be a limitation to any described method because array and mechanically scanned systems can be used interchangeably to perform the described methods.

Moreover, for both a mechanically scanned system and an array type system, transducers having a center frequency in a clinical frequency range of less than 20 MHz, or in a high frequency range of equal to or greater than 20 MHz can be used.

In the systems and methods described, an ultrasound mode or technique, such as "Power Doppler" can be used. The Power Doppler mode exploits the total power in the Doppler signal to produce color-coded real-time images of blood flow. The system and method can also be used to generate color Doppler images, which depict mean velocity information, or to generate B-Mode frames individually or as a collection describing a 3-D volume, Tissue Doppler, M-Mode acquisition of raw RF data, and to the application of molecular imaging with a contrast or image difference overlay.

For the application of molecular imaging, an image difference overlay can be used to highlight differences in intensity between a reference image and a data image. The heart beat and the respiration motion of a subject typically disturbs or moves an ultrasound image disallowing direct image subtraction to highlight differences in intensity. An exemplary method for creating an image difference overlay comprises identifying a loop of reference images of a subject or portion thereof. The method further comprises identifying a loop of data images of the subject or the portion thereof. A data image can be compared to a plurality of images of the reference image loop. At least one data image can be associated with at least one reference image. An image subtraction on the associated images can be performed to produce the image difference overlay. The data image can be associated with the at least one reference loop image based on similarity. For example, the similarity can be determined by summing the absolute difference of pixel intensity levels and associating the data loop image frame with the reference loop image frame or frames which yield the smallest absolute difference value. The methods described herein can be used along with overlay methods to enhance the ability of contrast overlay methods to highlight differences in intensity between a reference image and a data image In one exemplary aspect, the transducer can transmit ultrasound at a frequency of at least about 20 megahertz (MHz). In alternative aspects, for example and not meant to be limiting, the transducer can transmit ultrasound at or above about 20 MHz, 30 MHz, 40 MHz, 50 MHz, or 60 MHz. Further, transducer operating frequencies significantly greater than those mentioned are also contemplated.

Figure 2:
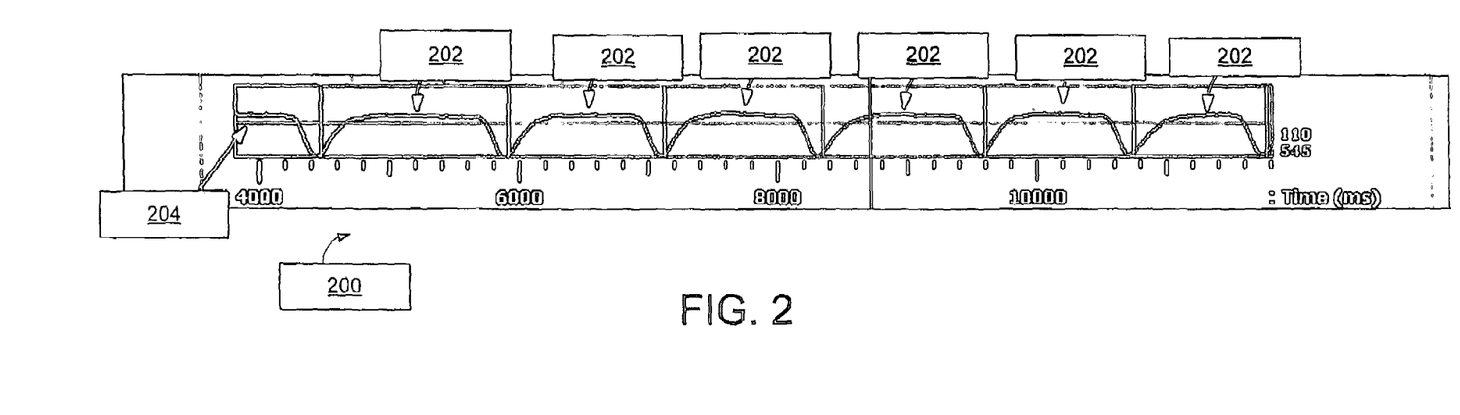
FIG. 2 shows an exemplary respiration waveform from an exemplary subject.

The subject 102 can be connected to electrocardiogram (ECG) electrodes 104 to obtain a cardiac rhythm and respiration waveform 200, see FIG. 2, from the subject 102. A respiration detection element 148, which includes respiration detection software 140, can be used to produce a respiration waveform 200 for provision to an ultrasound system 131. Respiration detection software 140 can produce a respiration waveform 200 by monitoring muscular resistance when a subject breathes. The use of ECG electrodes 104 and respiration detection software 140 to produce a respiration waveform 200 can be performed using a respiration detection element 148 and software 140 known in the art and available from, for example, Indus Instruments, Houston, Tex. In an alternative aspect, a respiration waveform can be produced by a method that does not employ ECG electrodes, for example, with a strain gauge plethysmograph.

The respiration detection software 140 converts electrical information from the ECG electrodes 104 into an analog signal that can be transmitted to the ultrasound system 131.

The analog signal is further converted into digital data by an analog-to-digital converter 152, which can be included in a signal processor 108 or can be located elsewhere, after being amplified by an ECG/respiration waveform amplifier 106. In one embodiment, the respiration detection element 148 comprises an amplifier for amplifying the analog signal for provision to the ultrasound system 131 and for conversion to digital data by the analog-to-digital converter 152. In this embodiment, use of the amplifier 106 can be avoided entirely. Using digitized data, respiration analysis software 142 located in memory 121 can determine characteristics of a subject's breathing including respiration rate and the time during which the subject's movement due to respiration has substantially stopped.

Cardiac signals from the electrodes 104 and the respiration waveform signals can be transmitted to an ECG/respiration waveform amplifier 106 to condition the signals for provision to an ultrasound system 131. It is recognized that a signal processor or other such device may be used instead of an ECG/respiration waveform amplifier 106 to condition the signals. If the cardiac signal or respiration waveform signal from the electrodes 104 is suitable, then use of the amplifier 106 can be avoided entirely.

An exemplary ultrasound system 131 having a mechanically scanned single element transducer includes a control subsystem 127, an image construction subsystem 129, sometimes referred to as a scan converter, a transmit subsystem 118, a receive subsystem 120, and a user input device in the form of a human machine interface 136. The processor 134 is coupled the control subsystem 127 and the display 116 is coupled to the processor 134.

Figure 9:
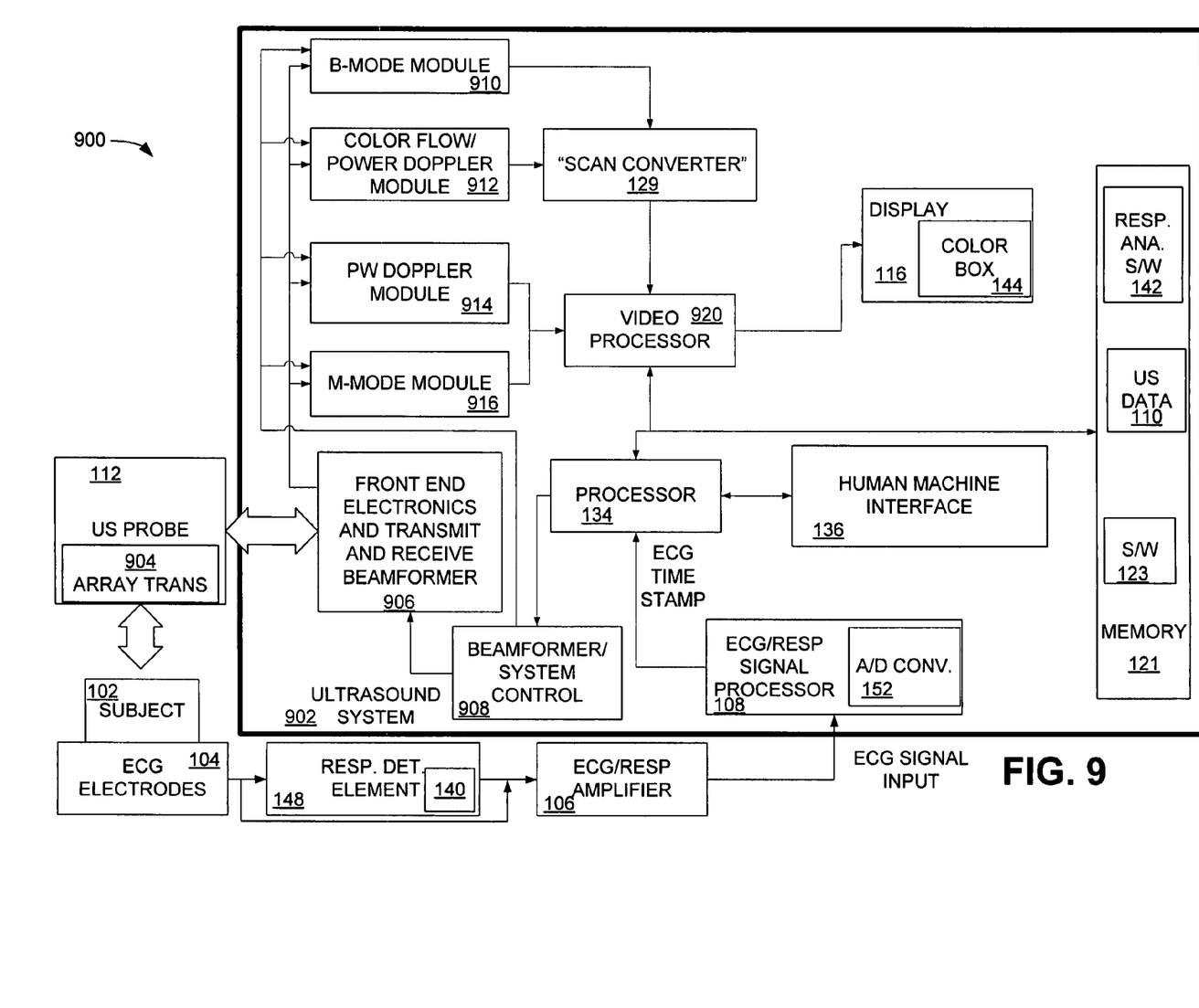
FIG. 9 is a block diagram illustrating an exemplary array based ultrasound imaging system.

An exemplary ultrasound system 902 having an array transducer 904 can include a processor 134, a front end electronics module 906, a transmit beamformer 906 and receive beamformer 906, a beamformer control module 908, processing modules for B-Mode 410, Color flow 912, Power Doppler 912, M-Mode 916, PW Doppler 914 and other modes such as Tissue Doppler and digital RF data, a scan converter 129, a video processing module 920 a display 116 and a user interface module 136.

A color box 144 can be projected to a user by the display 116. The color box 144 represents an area of the display 116 where Doppler data is acquired and displayed. The color box describes a region or predetermined area, within which, Power Doppler scanning is performed. The color box can also be generalized as defining the start and stop points of scanning either with a mechanically moved transducer or electronically as for an array based probe. The generalization extends to B-Mode images as well. The start and stop points of scanning can also define the edges of the B-Mode frame. The term "frame" can be used to describe a collection of lines for either B-Mode or Color Flow, Power Doppler or Tissue Doppler. The size or area of the color box 144 can be selected by an operator through use of the human machine interface 136, and can depend on the area in which the operator desires to obtain data. For example, if the operator desires to analyze blood flow within a given area of anatomy shown on the display 116, a color box 144 can be defined on the display corresponding to the anatomy area and representing the area in which the ultrasound transducer will transmit and receive ultrasound energy and data so that a user defined portion of anatomy can be imaged.

For a mechanically scanned transducer system, the transducer is moved from the start position to the end position, such as, for example a first scan position through an nth scan position. As the transducer moves, ultrasound pulses are transmitted by the transducer and the return ultrasound echoes are received by the transducer. Each transmit/receive pulse cycle results in the acquisition of an ultrasound line. All of the ultrasound lines acquired as the transducer moves from the start to the end position constitute an image "frame." For an ultrasound system which uses an array, the transmit beamformer, receive beamformer and front end electronics ultrasound pulses can be transmitted along multiple lines of sight within the color box. B-Mode data can be acquired for the entire field of view, whereas color flow data can acquired from the region defined by the color box.

The processor 134 is coupled the control subsystem 127 and the display 116 is coupled to the processor 134. A memory 121 is coupled to the processor 134. The memory 121 can be any type of computer memory, and is typically referred to as random access memory "RAM," in which the software 123 of the invention executes. Software 123 controls the acquisition, processing and display of the ultrasound data allowing the ultrasound system 131 to display an image.

The method and system for synchronization of breathing with the capture of ultrasound Doppler data can be implemented using a combination of hardware and software. The hardware implementation of the system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the system comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The exemplary mechanically scanned ultrasound system 131 software, comprising respiration analysis software 142, transducer localizing software 146 and system software 123 determines the position of the transducer 150 and determines the start and end positions of the transducer for ultrasound data signal acquisition. For an exemplary array system, a beamformer control module controls the position of the scan lines used for Power Doppler, Color Flow, or for other scanning modalities.

The respiration analysis software 142 allows capture of ultrasound data at the appropriate point during the respiration cycle of the subject 102. Thus, respiration analysis software 142 can control when ultrasound image data 110 is collected based on input from the subject 102 through the ECG electrodes 104 and the respiration detection software 140. The respiration analysis software 142 controls the collection of ultrasound data 110 at appropriate time points during the respiration waveform 200. For acquisition of Doppler data, in-phase (I) and quadrature-phase (Q) Doppler data can be captured during the appropriate time period when the respiration signal indicates a quiet period in the animal's breathing cycle. For acquisition of B-Mode data, the magnitude of the reflected signal is acquired by envelope detecting and log compressing the received RF data. By "quiet period" is meant a substantially non-motion period in the animal's respiratory or breathing cycle when the animal's motion due to breathing has substantially stopped. Thus, in the system described, the software 123, the respiration analysis software 142 and the transducer localizing software 146, or a beamformer control module/software for an array system, can control the acquisition, processing and display of ultrasound data, and can allow the ultrasound system 131 to capture ultrasound images at appropriate times during the respiration waveform of the subject 200. When the start of the quiet period is detected by the respiration analysis software, the transducer localizing software or beamformer control software/module sends a command causing the system to begin color flow acquisition.

In an alternative aspect, the system will initiate or trigger data acquisition after detecting a non-motion period of the subject and upon reaching a desired point in a concurrently monitored ECG waveform.

Memory 121 also includes the ultrasound data 110 obtained by the ultrasound system 131. A computer readable storage medium 138 is coupled to the processor for providing instructions to the processor to instruct and/or configure the processor to perform algorithms related to the operation of ultrasound system 131, as further explained below. The computer readable medium can include hardware and/or software such as, by the way of example only, magnetic disk, magnetic tape, optically readable medium such as CD ROMs, and semiconductor memory such as PCMCIA cards. In each case, the medium may take the form of a portable item such as a small disk, floppy disk, cassette, or may take the form of a relatively large or immobile item such as a hard disk drive, solid state memory card, or RAM provided in the support system. It should be noted that the above listed example mediums can be used either alone or in combination.

The ultrasound system 131 includes a control subsystem 127 to direct operation of various components of the ultrasound system 131. The control subsystem 127 and related components may be provided as software for instructing a general purpose processor or as specialized electronics in a hardware implementation. The ultrasound system 131 includes an image construction subsystem 129 for converting the electrical signals generated by the received ultrasound echoes to data that can be manipulated by the processor 134 and that can be rendered into an image on the display 116. The control subsystem 127 is connected to a transmit subsystem 118 to provide ultrasound transmit signal to the ultrasound probe 112. The ultrasound probe 112 in turn provides an ultrasound receive signal to a receive subsystem 120. The receive subsystem 120 also provides signals representative of the received signals to the image construction subsystem 129. The receive subsystem 120 is also connected to the control subsystem 127. The scan converter 129 for the image construction subsystem and for the respiration registration information is directed by the control subsystem 127 to operate on the received data to render an image for display using the image data 110.

The ultrasound system 131 may include the ECG/respiration waveform signal processor 108. The ECG/respiration waveform signal processor 108 is configured to receive signals from the ECG/respiration waveform amplifier 106 if the amplifier is utilized. If the amplifier 106 is not used, the ECG/respiration waveform signal processor 108 can also be adapted to receive signals directly from the ECG electrodes 104 or from the respiration detection element 148. The signal processor 108 can convert the analog signal from the respiration detection element 148 and software 140 into digital data for use in the ultrasound system 131. Thus, the ECG/respiration waveform signal processor can process signals that represent the cardiac cycle as well as the respiration waveform 200. The ECG/respiration waveform signal processor 108 provides various signals to the control subsystem 127. The receive subsystem 120 also receives ECG time stamps or respiration waveform time stamps from the ECG/respiration waveform signal processor 108. For example, each data sample of the ECG or respiration data is time registered with a time stamp derived from a clock.

The receive subsystem 120 is connected to the control subsystem 127 and an image construction subsystem 129. The image construction subsystem 129 is directed by the control subsystem 127. The ultrasound system 131 transmits and receives ultrasound data with the ultrasound probe 112, provides an interface to a user to control the operational parameters of the imaging system 100, and processes data appropriate to formulate still and moving images that represent anatomy and/or physiology of the subject 102. Images are presented to the user through the display 116.

The human machine interface 136 of the ultrasound system 131 takes input from the user and translates such input to control the operation of the ultrasound probe 112. The human machine interface 136 also presents processed images and data to the user through the display 116. Using the human machine interface 136 a user can define a color box 144, or optionally, the user can extend image acquisition to a fuller field of view. A fuller field of view can be used for acquisition of a B-Mode frame. Optionally, the extent can be configured automatically based on predefined desired image size parameters such as field of view. Thus, at the human machine interface 136, the user can define the color box 144 which represents the area in which image data 110 is collected from the subject 102. The color box 144 defines the area where the ultrasound transducer 150 transmits and receives ultrasound signals. Software 123 in cooperation with respiration analysis software 142 and transducer localizing software 146, or in the case of an array system, a beamformer control module/software, and in cooperation with the image construction subsystem 129 operate on the electrical signals developed by the receive subsystem 120 to develop an ultrasound image which is acquired at specific intervals within the respiratory cycle corresponding to the breathing or respiration waveform of the subject 102.

FIG. 2 shows an exemplary respiration waveform 200 from a subject 102 where the x-axis represents time in milliseconds (ms) and the y-axis represents voltage in millivolts (mV). A typical respiration waveform 200 includes multiple peaks positions or plateaus 202, one for each respiration cycle of the subject. As shown in FIG. 2, a reference line 204 can be inserted on the waveform 202. The portions of the respiration waveform 200 above the reference line 204, are peaks or plateaus 202, and generally represent the period when the subject's movement due to breathing has substantially stopped, i.e., a "motionless" or "non-motion" period.

By "substantially stopped" is meant that a subject's movement due to breathing has stopped to the point at which the collection of Doppler ultrasound data is desirable because of a reduction in artifacts and inaccuracies that would otherwise result in the acquired image due to breathing motion.

It is to be understood that depending on the recording equipment used to acquire respiration data and the algorithmic method used to analyze the digitalized signal, the motionless period may not align perfectly with the detected signal position. Thus, time offsets may be required to be used that are typically dependent on the equipment and detection method used and animal anatomy. For example, in one exemplary recording technique, using the muscular resistance of the foot pads, the motionless period starts shortly after the detected peak in resistance. One skilled in the art can appreciate that the determination of the actual points in the respiration signal, regardless of how it is acquired, can be easily determined by empirical comparison of the signal to the actual animals motion and choosing suitable corrections such that the signal analysis performed can produce an event describing the respective start and stop points of respiration motion.

A subject's motion due to breathing substantially stops for a period of approximately 100 to 2000 milliseconds during a respiration cycle. The period during a subject's respiration cycle during which that subject's motion due to breathing has substantially stopped may vary depending on several factors including, animal species, body temperature, body mass or anesthesia level. The respiration waveform 200 including the peaks 202 can be determined by the respiration detection software 140 from electrical signals delivered by ECG electrodes 104 which can detect muscular resistance when breathing. For example, muscular resistance can be detected by applying electrodes to a subject's foot pads.

By detecting changes in muscular resistance in the foot pads, the respiration detection software 140 can generate the respiration waveform 200. Thus, variations during a subject's respiration cycle can be detected and ultrasound data can be acquired during the appropriate time of the respiration cycle when the subject's motion due to breathing has substantially stopped. For example, Doppler samples can be captured during the approximate 100 milliseconds to 2000 millisecond period when movement has substantially ceased. A respiration waveform 200 can also be determined by the respiration detection software 140 from signals delivered by a pneumatic cushion (not shown) positioned underneath the subject. An exemplary use of a pneumatic cushion to produce signals from a subject's breathing is known in the art.

Figure 3:
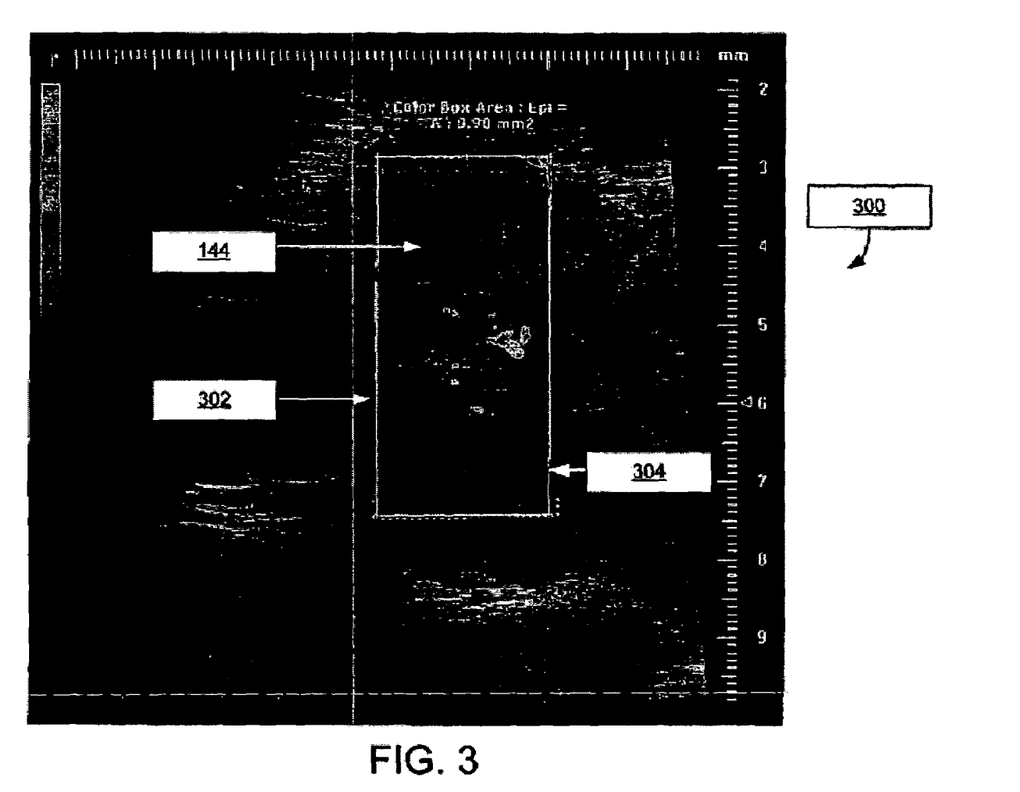
FIG. 3 shows an exemplary display of FIG. 1 with an exemplary color box of FIG. 1.

FIG. 3 shows an exemplary display 116 of the ultrasound imaging system 131 with an exemplary color box 144. The image 300 represents an image displayed on the display 116. The color box 144 is defined within the image 300. The color box 144 represents an area of the ultrasound image 300 on the display 116 that corresponds to a portion of the subject's anatomy where ultrasound data is collected by the ultrasound probe 112. As will be understood to one skilled in the art, multiple color boxes 144 can also be defined simultaneously on the display or at different times and such multiple color boxes 144 can be used in the methods described.

The area encompassed by the color box 144 can be defined by a user via the human machine interface 136 or configured automatically or semi-automatically based on a desired predefined image size such as filed of view (FOV) as is typically the case for B-Mode acquired data. Thus, the color box 144 represents an area where data is captured and depicted on the display 116. The image data 110 is collected within the color box 144 by registering the transducer 150 of the ultrasound probe 112 within the color box 144. The ultrasound transducer 150 can be a single element sweeping transducer or an electronically scanned transducer such as a linear, focused, or phased array. The ultrasound transducer 150 can be located anywhere on the anatomy that corresponds to a defined color box 144. The transducer localizing software 146 can be used to localize the transducer 150 at any defined location within the color box 144.

The initial position of the transducer 150 can define a starting point for transmitting and acquiring ultrasound energy and data. Thus, in one example, the transducer 150 can be located at the left side 302 of the color box 144 and ultrasound energy and data can be transmitted and received starting at the left side of the color box. Similarly, any portion of the color box 144 can be defined as an end point for transmitting and acquiring ultrasound energy and data. For example, the right side 304 of the color box 144 can be defied as an end point for transmitting and acquiring ultrasound energy and data. Ultrasound energy and data can be transmitted and received at any point and time between the starting and end point of the color box. Therefore, in one aspect of the invention, a user can define the left side 302 of a color box 144 as the starting point and the right side 304 of the same color box 144 as an end point. In this example, ultrasound energy and data can be transmitted and received at any point and time between the left side 302 of the color box 144 and moving towards the right side 304 of the color box 144. Moreover, it would be clear to one skilled in the art that any side or region of a color box 144 could be defined as the starting point and any side or region of a color box 144 could be defined as an end point.

It is to be understood that all references to motion using a mechanically positioned transducer are equally analogous to suitable configuration of the beamformer in an array based system and that these methods described herein are applicable to both systems. For example, stating that the transducer should be positioned at its starting point, is analogous to stating that the array beamformer is configured to receive ultrasound echoes a start position.

Figure 4:
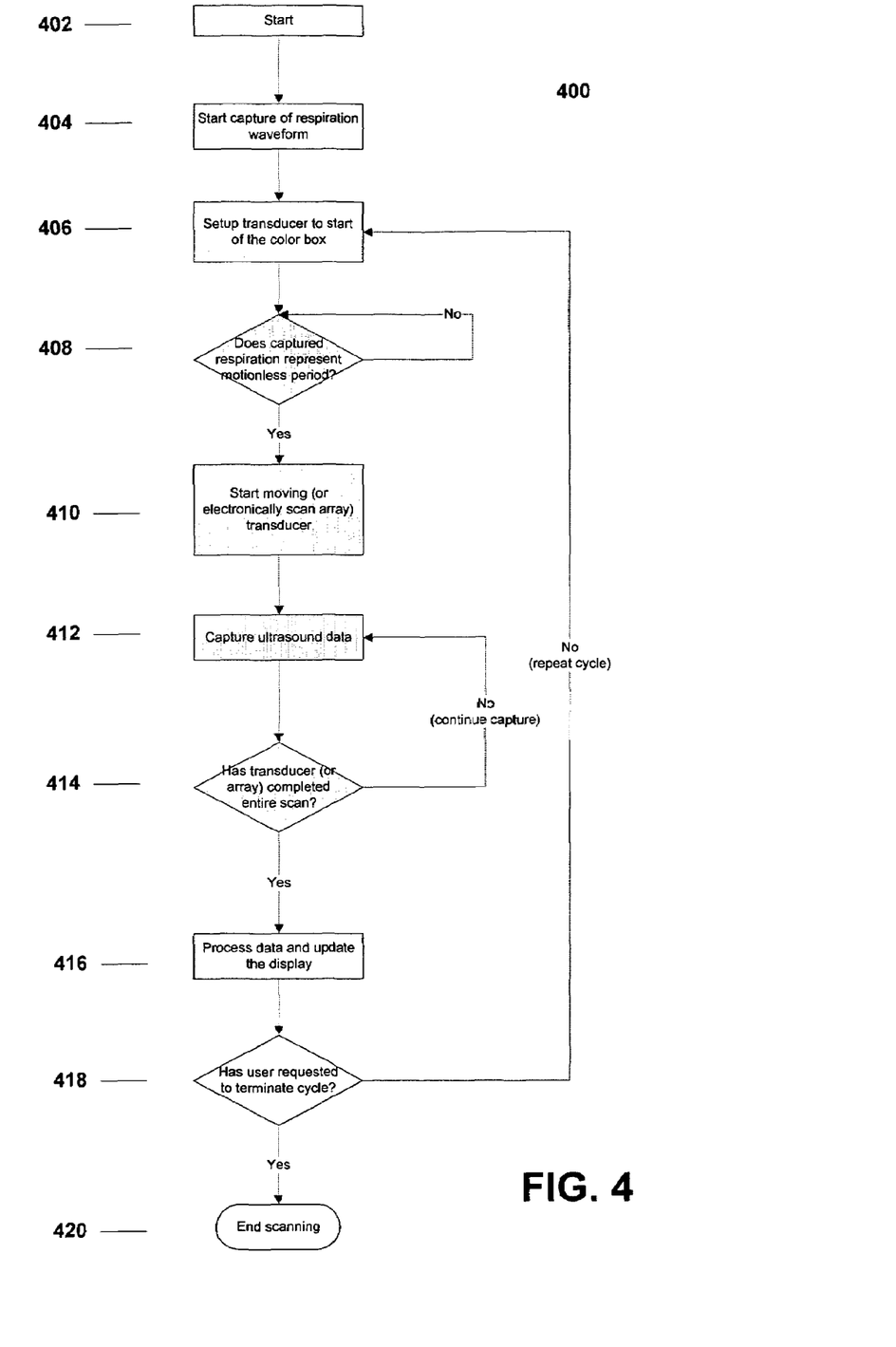
FIG. 4 is a block diagram illustrating an exemplary method of producing an ultrasound image using the exemplary system of FIG. 1.

FIG. 4 is a flowchart illustrating an exemplary method of producing an ultrasound image using the exemplary imaging system 100. As would be clear to one skilled in the art, and based on the teachings above, the method described could be performed using an alternative exemplary imaging system.

At a start position 402, a single element transducer 150 or an array transducer 704 is placed in proximity to a subject 102. In block 404, a respiration waveform 200 from the subject 102 is captured by respiration detection software 140. IN one aspect, the respiration waveform 200 is captured continuously at an operator selected frequency. For example, the respiration waveform can be digitized continuously at 8000 Hz. In block 406, once the transducer 150 is placed in proximity to the subject 102, the transducer is positioned at a starting position in the color box 144. In one embodiment, the transducer is positioned at the left side 302 of the color box 144 when the color box is viewed on the display 116. However, any side or region of a color box could be defined as the starting point and any side or region of a color box could be defined as an end point.

In step 408, the respiration analysis software 142 determines if a captured sample represents the start of the motionless period 202 of the respiration waveform 200. One skilled in the art will appreciate that the point at which the motionless or non-motion period begins is not necessarily the "peak" of the respiratory waveform; also, the point in the waveform which corresponds to the motionless period can be dependent on the type of method used to acquire the respiratory waveform. A captured sample of the continuously captured respiration waveform 200 represents the value of the captured respiration waveform 200 at a point in time defined by the selected sampling frequency. At a particular point 202 of the subject's respiration waveform 200, the subject's movement due to breathing has substantially stopped. This is a desired time for image data to be captured. As noted above, a mechanically moved transducer or an array transducer can be used for collection of ultrasound data.

Prior to the initialization of Color Flow, Power Doppler, or B-Mode scanning, the transducer can be positioned at the start point defined by the color box. In block 410, if respiration analysis software 142 determines that the subject 102 is at a point which represents the beginning of the motionless period 202 of its respiration cycle, the transmit subsystem 118, under the control of the software 123 causes the transducer 150 to start moving. If the captured sample at block 406 does not represent a peak 202 of the subject's respiration cycle, the respiration detection software 142 continues to monitor for a respiration peak 202.

In block 412, the transducer begins scanning, and ultrasound data is acquired. For a mechanically scanned transducer system, the speed of motion can be set such that it completes the entire scan from start to stop within the motionless period of the respiration cycle. In block 414, the completion of the frame is checked. If frame completion has not occurred, the process loops back to block 412, and scanning continues. If the completion of frame has occurred, then scanning stops, the data is processed and the display is updated in block 416. After the display has been updated, in block 418 the system software checks for a user request to terminate imaging. In block 420, if the image termination request has occurred, imaging stops. If, in block 418, no termination request has been made, the process loops back to block 406.

The period of time during which ultrasound samples are captured can vary depending on the subject's respiration cycle. For example, ultrasound samples can be collected for a duration of between about 200 to about 2000 milliseconds. Ultrasound I and Q data can be captured during the quiet period in the subject's respiration cycle for Doppler acquisition. Envelope data can be acquired for B-Mode. For example, 200 milliseconds is an estimate of the period of time which a subject 102 may be substantially motionless in its respiration cycle 200. This substantially motionless period is the period when the ultrasound samples are collected.

Figure 5:
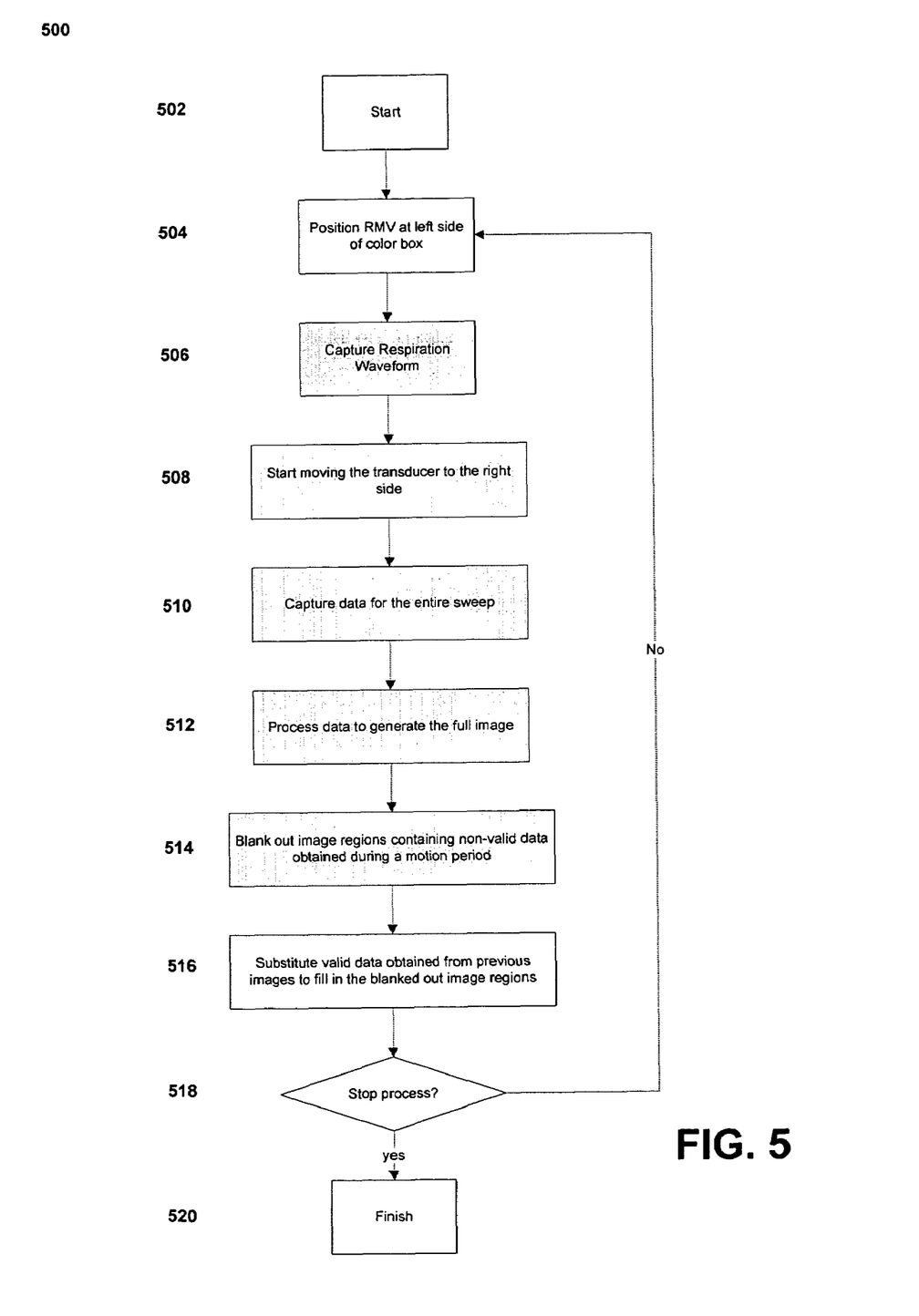
FIG. 5 is a block diagram illustrating an exemplary method of producing an ultrasound image using the exemplary system of FIG. 1.

FIG. 5 is a flowchart 500 illustrating an alternative method of producing an image using the exemplary imaging system 100. As will be clear to one skilled in the art, and based on the teachings above, the method described could be performed using an alternative exemplary imaging system. The method 500 uses the same hardware as the method 400, and can use respiration analysis software 142 and transducer localizing software 146 programmed according to the noted modes and methodologies described herein. As with method outlined in flowchart 400, the transducer can be positioned at the left side 302 of the color box 144. Or, in the case of an array based system, the beamformer can be configured to begin scanning at the left side of the color box. It will be clear to one skilled in the art that any side or region of a color box could be defined as the starting point and any side or region of a color box could be defined as an end point.

In block 504, the transducer is placed at the left side 302 of the color box. In block 506, a respiration waveform is captured. The respiratory waveform can be time stamped, such that there is known temporal registration between the acquired ultrasound lines and the respiratory waveform. This form of scanning involves time registration of the respiratory waveform. A new frame can be initiated as soon as the previous one ends. Therefore, the respiratory waveform and the start of frame may not be synchronous. The time period during which maximum level of respiratory motion occurs, the motion period, is determined from the respiratory waveform using the respiratory analysis software. Data which is acquired during this time period is assumed to be distorted by respiratory motion and is termed "non-valid" data. Data acquired during the motionless phase of the respiratory cycle is termed "valid" data. In various exemplary aspects, the non-valid data can be replaced with valid data from the same region acquired during a previous frame, or with data obtained by processing valid data acquired during previous frames using an averaging or persistence method.

In block 508, software 123 causes the transducer to start moving to the right side 304 of the color box and performs a complete sweep of the color box.

A mechanically moved transducer 150 or an array transducer 704 can be used for collection of ultrasound data. In block 510, ultrasound data is captured for the entire sweep or translation across the color box 508. In block 512, the data is processed to generate an initial image. In block 514, the respiratory waveform is processed to determine the "blanked period," which corresponds to the period during which there is high respiratory motion in the subject and the regions of the image, or lines within the frame, which occurred during the "blanked period" are determined from the time stamp information. These lines of which were acquired during the "blanked period" are not displayed. Instead, the lines in the blanked region are filled in. There are various methods which can be used to fill in the blanked regions. For example, previously acquired frames can be stored in a buffer in memory, and the video processing software can display lines from previously acquired frames which correspond to the blanked out lines. Thus, in block 516, data from a previous image frame can be used to fill in areas blanked out in block 514.

In one exemplary aspect, the process for producing an ultrasound image outlined in FIG. 5 comprises monitoring a respiration waveform of a subject and detecting at least one peak period and at least one non-peak period of the respiration waveform. In this aspect, each peak period corresponds to a time when the subject's bodily motion caused by its respiration has substantially stopped and each non-peak period corresponds to a time when the subject's body is in motion due to its respiration. The process further comprises generating ultrasound at a frequency of at least 20 megahertz (MHz), transmitting ultrasound at a frequency of at least 20 MHz into a subject, and acquiring ultrasound data during the least one peak period of the subject's respiration waveform and during the at least one non-peak period of the subject's respiration waveform. In exemplary aspect, the steps of generating, transmitting and acquiring are incrementally repeated from a first scan line position through an nth scan line position.

In this example, the received ultrasound data are complied to form an initial image. At least one portion of the initial image comprising data received during a non-peak period of the subject's respiration waveform is identified and processed to produce the final ultrasound image. In this aspect, the final ultrasound image is compiled from data received during the incremental peak periods of the subject's respiration waveform.

In aspects of this example, the processing step comprises removing data, i.e., "non-valid" data, from the initial image that was received during non-peak periods of the subject's respiration waveform to produce a partially blanked out image having at least one blanked out region and substituting data, i.e., "valid" data, received during the peak of the subject's respiration waveform from another initial image into the at least one blanked out region of the partially blanked out image to produce the ultrasound image.

In one aspect, persistence can be applied to color flow image data. As one skilled in the art will appreciate, persistence is a process in which information from each spatial location in the most recently acquired frame is combined according to a algorithm with information from the corresponding spatial locations from previous frames. In one aspect, persistence processing may occur in the scan converter software unit. An exemplary persistence algorithm that can be used is as follows:

$$Y(n)=\alpha Y(n-1)+(1-\alpha)X(n),$$

where Y(n) is the output value which is displayed, X(n) is the most recently acquired Power Doppler sample, Y(n−1) is the output value derived for the previous frame, and $\alpha$ is a coefficient which determines the amount of persistence. When there are non-valid or blanked regions in the most recently acquired image frame, persistence can be applied to the entire frame, with the non-valid lines being given a value of zero. Provided that the start of frame of each Power Doppler frame is not synchronous with the respiratory waveform, the non-valid time periods occurs at different times within each frame.

Another exemplary method of handling the non-valid or blanked regions is to implement persistence on a line to line basis. For lines which have a valid value, persistence is implemented as above. For lines which are determined to be within the non-valid region, the persistence operation is suspended. Thus, in the above equation, instead of setting X(n) to zero and calculating Y(n), Y(n) is set equal to Y(n−1).

In block 518, it is determined whether to stop the process. In one aspect, the condition to stop the process is met when the position of the transducer meets or exceeds the stop position of the color box 144. In an alternative aspect, the process can continue until an operator issues a stop command. If, in block 518, it is determined that the process is not complete, the transducer is repositioned at the left side 302 of the color box. If in block 518, it is determined that the process is finished, the process is complete at block 520. The blanking process described in block 514 and 516 is optional. In some cases, if for example the rate at which the transducer moves across the anatomy is high, the entire data set may be acquired without a respiration event occurring. In these cases, image blanking is not performed.

Figure 6:
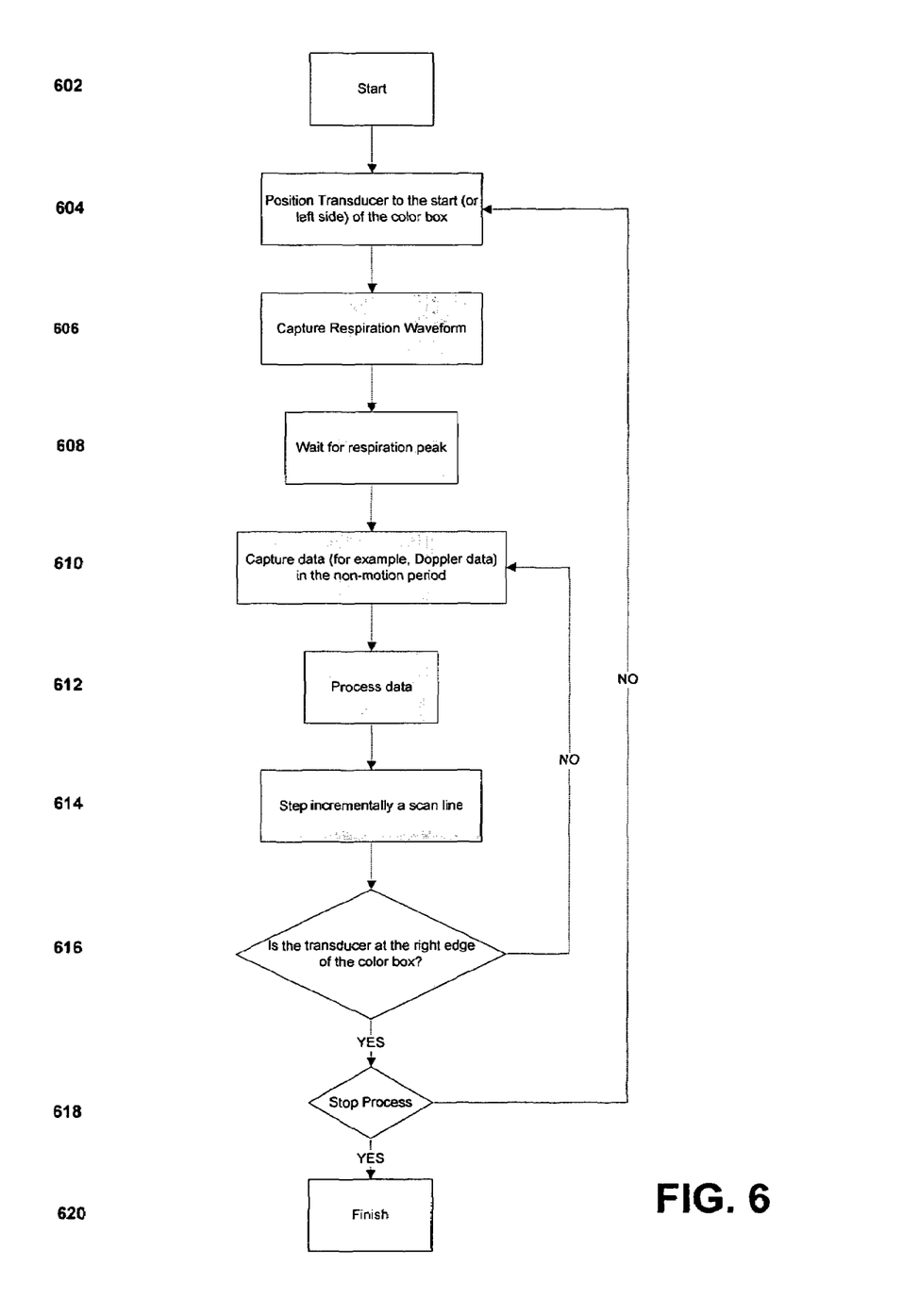
FIG. 6 is a block diagram illustrating an exemplary method of producing an ultrasound image using the exemplary system of FIG. 1.

FIG. 6 is a flow chart illustrating another exemplary embodiment 600 for producing an image using the imaging system 100. As will be clear to one skilled in the art, and based on the teachings above, the method described could be performed using an alternative exemplary imaging system. In this method, the transducer 150 is moved once per respiration cycle. A mechanically moved transducer can be used for collection of ultrasound data. Thus, in this method, one line of data is captured when the subject's movement due to respiration has substantially stopped. Once this substantially motionless period ends, the transducer recaptures image data the next time in the subject's respiration cycle when the subject is substantially motionless again. Thus, one line of data is captured per respiration cycle when the subject is substantially still.

The method 600 begins at block 602. In block 604, a transducer is positioned at the start of the color box 144. In one example, the left side 302 of the color box 144 can be defined as start point for the transducer and the right side 304 can be defined as the end point. In block 606, a respiration waveform is captured from the subject 102 using ECG electrodes 104 and respiration detection software 140. In block 608, respiration analysis software 142 analyzes the respiration waveform and instructs the ultrasound system 131 to wait for a respiration peak 202.

In block 610, ultrasound samples are captured in the quiet time or period of the respiration wave approximately 100 to 200 milliseconds after the respiration peak detected in block 608. The quiet period depends on the period of the subject's respiration. For example, in a mouse, the quiet period can be approximately 100 to 200 milliseconds. Doppler I and Q data can be captured during the quiet period in the animal's respiration cycle or optionally acquisition of envelope data is acquired for B-Mode. In block 612, captured ultrasound Doppler data is processed by the ultrasound system 131, and in block 614 a step motor moves the transducer 150 a small distance through the color box 144. In block 616, it is determined whether the transducer is at the end 304 of the color box 144. If it is determined that the transducer is not at the end 304 of the color box 144, an ultrasound sample data captured during a peak 202 of the respiration waveform. If it is determined that the transducer is at the right edge 304 of the color box, it is further determined at block 618 whether to stop the process. If the transducer is at the right edge 304 of the color box the process is stopped. If it is determined that the process is to be stopped, the process is finished. If it is determined that the process is not finished because the transducer is not at the right edge 304 of the color box, the transducer is repositioned to the start or left side 302 of the color box.

Figure 7:
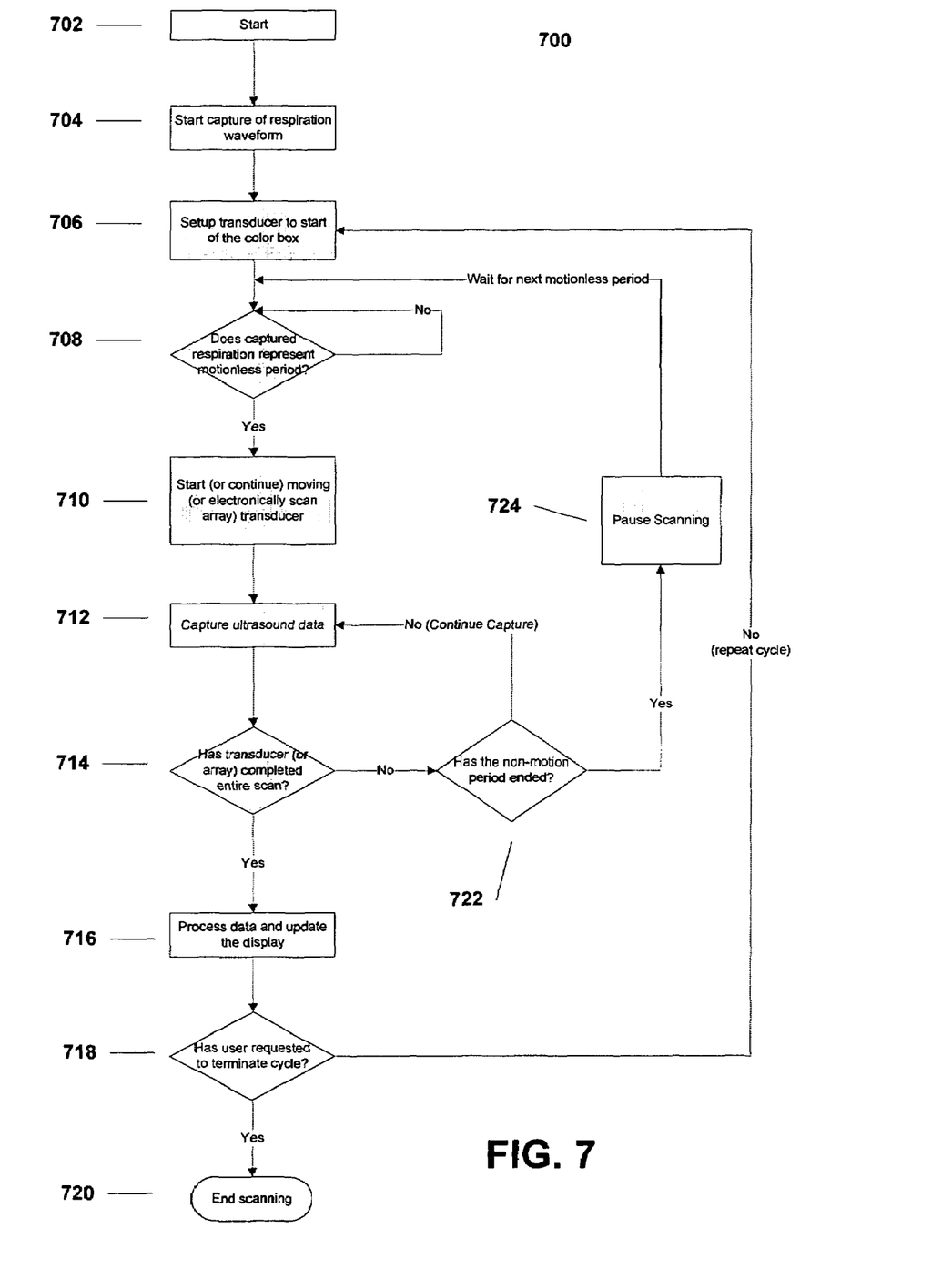
FIG. 7 is a block diagram illustrating an exemplary method of producing an ultrasound image using the exemplary system of FIG. 1.

In another embodiment of this method, shown in FIG. 7, if the system detects that the motionless period of the respiration cycle has ended the motion of the transducer can be paused in mid-frame. The transducer can remain at this position until the beginning of the next motionless period is detected at which time scanning can resume.

This embodiment is primarily applicable to the mechanically scanned transducer system. As described previously in flowchart 400 and as shown in FIG. 4, an embodiment is illustrated wherein the speed of the motor is set such that the entire frame is captured during the motionless period of one respiration cycle. The embodiment described in flowchart 700 permits the acquisition of one frame over multiple heart cycles.

After the user requests that imaging commence in block 702, the respiratory waveform acquisition is started, block 704. In block 706, the transducer is positioned at the start or side 302 of the color box 144. Once the beginning of the motionless period is detected in block 708, the transducer begins moving, block 710, and ultrasound data is acquired, block 712. In block 714, the transducer localizing software 146 determines if the transducer is at the other (end) limit 304 of the color box 144. If the transponder is at the end limit, the ultrasound data is processed and the display 116 is updated in block 716. Next, in block 720, the system software 123 will check whether the user has requested termination of imaging. If true, no further scanning is undertaken until the user requests that imaging begin. If the user has not requested termination of imaging, then the process loops back to block 704, in which the transducer is positioned at the start of the color box 144.

In this exemplified aspect, if, in block 714, it is determined that the transducer motion has not reached the end of frame it is then tested in block 722 as to whether the respiration cycle has reached the end of the motionless period. If we are still in the motionless period scanning and capture of ultrasound data continues in block 712. Otherwise, in block 724, the scanning is paused and proceeds to block 708 where the system waits for the start of the next motionless period. When this "motionless" condition is met, the process loops back to block 710 and continues scanning.

Figure 8:
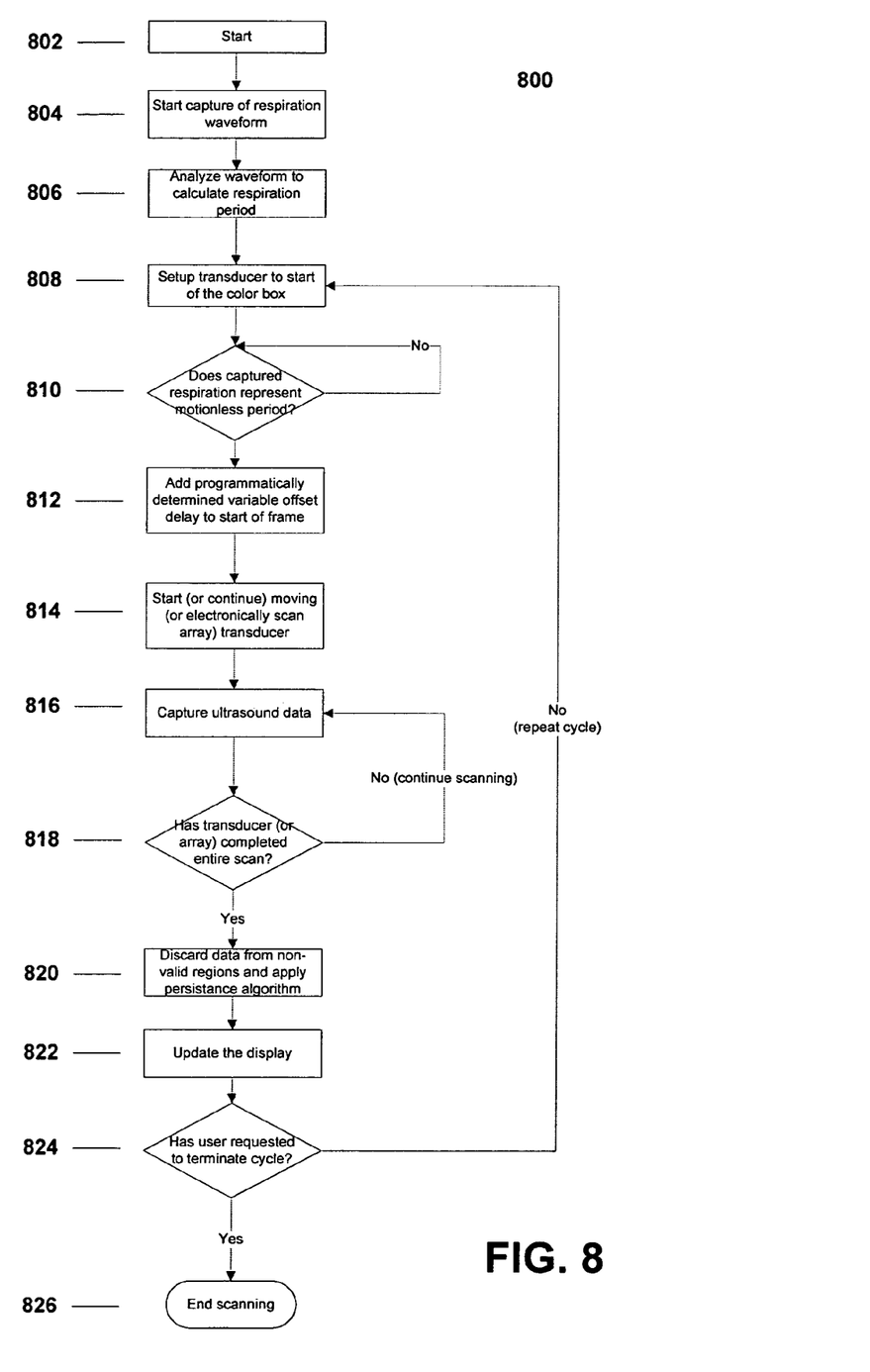
FIG. 8 is a block diagram illustrating an exemplary method of producing an ultrasound image using the exemplary system of FIG. 1.

FIG. 8 is a flowchart 800 illustrating another method of producing an image using the exemplary imaging system 100. As would be clear to one skilled in the art, and based on the teachings above, the method described could be performed using an alternative exemplary imaging system. This embodiment is intended to alter the timing of the start of frame with respect to the motion periods from frame to frame of the respiration cycle in order to minimize the likelihood of overlap of the non-valid regions in successive frames.

At a start position 802, a single element transducer 150 or an array transducer 704 is placed in proximity to a subject 102. In block 804, a respiration waveform 200 from the subject 102 is captured by respiration detection software 140. The respiration waveform 200 is captured continuously at an operator selected frequency. For example, the respiration waveform can be digitized continuously at 8000 Hz. In block 806 the respiration signal is analyzed to determine the current respiration period (Tr). This analysis continues throughout the acquisition such that Tr is continuously updated with the current respiration rate. In block 808, once the transducer 150 is placed in proximity to the subject 102, the transducer is positioned at a starting position in the color box 144. In step 810, the respiration analysis software 142 determines if a captured sample represents the start of the motionless period 202 of the respiration waveform 200. At a particular point 202 of the subject's respiration waveform 200, the subject's movement due to breathing has substantially stopped. This is a desired time for image data to be captured. A mechanically moved transducer or an array transducer can be used for collection of ultrasound data.

It is contemplated that, prior to the initialization of Color Flow, Power Doppler, or B-Mode scanning, the transducer can be positioned at the start point defined by the color box. In block 812, if respiration analysis software 142 determines that the subject 102 is at a point which represents the beginning of the motionless period 202 of its respiration cycle, a programmatically determined offset delays the transducers 150 start motion command. If the captured sample at block 810 does not represent a peak 202 of the subject's respiration cycle, the respiration detection software 142 continues to monitor for a respiration peak 202.

The programmatically determined offset values are used to delay the start of frame relative to the beginning of the motionless period. A set of N delay values Td, which are derived from Tr, where $0 \leq Td < Tr$, is stored in memory. The delay values, Td, are applied in sequence, and when the final delay is applied, the sequence starts again from the beginning. For example, the set of delays may consist of the values (0, Tr/2). The delays applied to a succession of frames would then be 0, Tr/2, 0, Tr/2. Or for example, the delays may consist of the values (0, Tr/3, 2×Tr/3). In another aspect, the delays may be generated by the equation $$Td = modulo(n, N) \times Tr/N$$

where modulo is the modulus operation and the statement modulo (4,3) would equal "1" and N is the number of values in the sequence. Alternatively, one will appreciate that it is contemplated that the delay values can be derived by another conventional method.

In block 814, the transducer begins scanning, and ultrasound data is acquired in box 816. In block 818, the completion of the frame is checked. If frame completion has not occurred, the process loops back to block 816, and scanning continues. However, if the completion of frame has occurred, then scanning stops. In box 820, the time period during which maximum level of respiratory motion occurs is determined from the respiratory waveform using the respiratory analysis software. As noted above, data that is acquired during this time period is assumed to be distorted by respiratory motion and is termed "non-valid" data and data acquired during the motionless phase of the respiratory cycle is termed "valid" data. The non-valid data is replaced with valid data from the same region acquired during a previous frame, or with data obtained by processing valid data acquired during previous frames using an averaging or persistence method. This replication method has been described previously as part of flowchart 500.

Subsequently, the data is processed and the display is updated in block 822. After the display has been updated, in block 824 the system software checks for a user request to terminate imaging. In block 826, if the image termination request has occurred, imaging stops. If, in block 418, no termination request has been made, the process loops back to block 406.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

What is claimed is:

1. A method for producing an ultrasound image, comprising:

monitoring a respiration waveform of a subject and detecting at least one substantially non-motion period in the respiration waveform, each non-motion period corresponding to a time when the subject's bodily motion caused by its respiration has substantially stopped, and at least one motion period of the respiration waveform, each motion period corresponding to a time when the subject's body is in motion due to its respiration;

generating ultrasound at a frequency of at least 20 megahertz (MHz);

transmitting ultrasound at a frequency of at least 20 MHz into a subject;

acquiring ultrasound data during the at least one non-motion period of the subject's respiration waveform and during the at least one motion period of the subject's respiration waveform, wherein the steps of generating, transmitting and acquiring are incrementally repeated from a first scan line position though an nth scan line position;

compiling the received ultrasound data to form an initial image;

identifying at least one portion of the initial image comprising data received during a motion period of the subject's respiration waveform; and processing the initial image to produce the ultrasound image, wherein the processing step comprises:

removing non-valid data from the initial image that was received during motion periods of the subject's respiration waveform to produce a partially blanked out image having at least one blanked out region; and substituting valid data received during the non-motion period of the subject's respiration waveform from another initial image formed in the above manner into the at least one blanked out region of the partially blanked out image to produce the ultrasound image.

2. The method of claim 1, wherein the subject is a laboratory animal.

3. The method of claim 2, wherein the laboratory animal is a mouse or a rat.

4. The method of claim 1, wherein the ultrasound is generated in a frequency range of about 20 MHz to about 60 MHz.

5. The method of claim 1, wherein the ultrasound image is a blood flow image of a laboratory animal.

6. The method of claim 1, further comprising repeating the steps of generating, transmitting and acquiring for a predetermined number of breaths of the subject.

7. The method of claim 1, further comprising repeating the steps of generating, transmitting and acquiring for a predetermined time period.

8. The method of claim 1, wherein the mode of the ultrasound image is selected from a group consisting of: B-Mode, Color Flow, Power Doppler, M-Mode, PW Doppler, contrast imaging, and Tissue Doppler.

9. The method of claim 1, wherein the step of monitoring a respiration waveform of a subject comprises:

detecting a peak in the respiration waveform; and determining a respiratory period of the respiratory waveform, wherein the peak and the respiratory period can be used to predict a beginning and an end of the substantially non-motion period in the waveform.

10. The method of claim 9, further comprising, after the monitoring step:

predicting the beginning of the non-motion period, based on acquisition and analysis of the respiration waveform, and triggering the initiation of the steps of generating, transmitting, and acquiring to substantially coincide with the beginning of the non-motion period, whereby imaging is synchronized with the respiration waveform.

11. The method of claim 1, wherein the processing step further comprises applying a persistence algorithm to derive valid data for substitution into the respective blanked out regions.

12. The method of claim 1, wherein the steps of generating, transmitting, and acquiring are incrementally repeated for one scan line position of the first scan line position through nth scan line position for each sequential non-motion period.

13. The method of claim 8, wherein said mode is Power Doppler.

* * * * *